United States Patent [19]

Sullivan et al.

[11] Patent Number: 6,075,171
[45] Date of Patent: Jun. 13, 2000

[54] 2-SUBSTITUTED 7-HALOINDENES AND METHODS FOR SYNTHESIZING

[75] Inventors: Jeffrey M. Sullivan, Loveland; Hamlin H. Barnes, Fort Collins, both of Colo.

[73] Assignee: Boulder Scientific Company, Mead, Colo.

[21] Appl. No.: 09/155,176

[22] PCT Filed: Feb. 5, 1998

[86] PCT No.: PCT/US98/02345

§ 371 Date: Sep. 22, 1998

§ 102(e) Date: Sep. 22, 1998

[87] PCT Pub. No.: WO98/33752

PCT Pub. Date: Aug. 6, 1998

Related U.S. Application Data

[63] Continuation-in-part of application No. 08/795,019, Feb. 5, 1997, Pat. No. 5,789,634.

[51] Int. Cl.$^7$ .............................. C07C 22/00; C07C 25/00
[52] U. S. Cl. .............................................. 570/129; 570/183
[58] Field of Search ..................................... 570/129, 183

[56] References Cited

U.S. PATENT DOCUMENTS 5,789,634  8/1998  Sullivan et al. .

*Primary Examiner*—Paul J. Killos
*Attorney, Agent, or Firm*—Edward S. Irons

[57] ABSTRACT

Novel 2-substituted 7-haloindenes and methods for synthesizing such indents are described. The 2-substituted 7-haloindenes may be coupled with any aryl group to produce a metallocene catalyst intermediate.

13 Claims, 4 Drawing Sheets

2-SUBSTITUTED 7-HALOINDENES AND METHODS FOR SYNTHESIZING

This application is a continuation-in-part of application Ser. No. 08/795,019 filed Feb. 5, 1997, now U.S. Pat. No. 5,789,634.

FIELD OF THE INVENTION

This invention relates to 2-substituted 7-haloindenes useful in coupling reactions to produce a wide variety of metallocene olefin polymerization catalyst intermediates and to metallocene catalysts derived from such intermediates.

BACKGROUND OF THE INVENTION

Metallocenes which comprise indene systems are well known $\alpha$-olefin polymerization catalysts. Substitution patterns in such indene systems significantly influence poly-$\alpha$-olefin properties, including tacticity and molecular weight.

Spaleck, et al., *Organometallics* (1994) 13:954–963 describes bridged zirconocene catalysts including indene systems illustrated by Compound 4 of "Scheme 1" (p. 955) which yield highly isotactic polypropylene when used with methylaluminoxane as a cocatalyst. As shown by "Scheme 2", Compound 10, Spaleck's synthesis requires an expensive 2-(bromomethyl) biphenyl starting material.

This invention provides a more cost effective synthesis of metallocene catalysts which comprise indene systems.

SUMMARY OF THE INVENTION

One aspect of this invention provides novel 2-substituted, 7-haloindenes of Formula I:

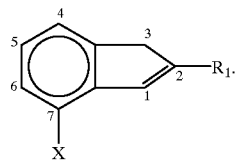

I in which $R_1$ is any straight or branched chain alkyl group having 1 to 10 carbon atoms, and X is a halogen, i.e., fluorine, chlorine, bromine or iodine. A preferred embodiment of this aspect of the invention is 2-methyl-7-chloroindene.

Another aspect of the invention includes coupling of Formula I indenes with a Grignard reagent having the formula ArMgX to produce the novel compounds of Formula II:

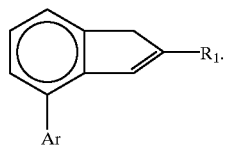

II in which Ar may be any aryl group preferably a phenyl, or a napthyl. Formula II compounds in which Ar is a phenyl, e.g., Spaleck's compounds 13a and 13b, or a naphthyl group are useful for the synthesis of the zirconocene olefin polymerization catalysts of Spaleck's "Scheme 1". See Spaleck compounds 7a, 7b, 7c, 8 and 9.

The invention accordingly comprises the novel Formula I and II compounds per se, procedures for the synthesis thereof, procedures for the conversion of Formula II compounds to catalyst intermediates, including Spaleck's compounds 13a and 13b, for the production of metallocene catalysts from such intermediates and for the use of such catalysts to polymerize, e.g., an $\alpha$-olefin.

DETAILED DESCRIPTION OF THE INVENTION PREPARATION OF FORMULA I COMPOUNDS

Figure 1:
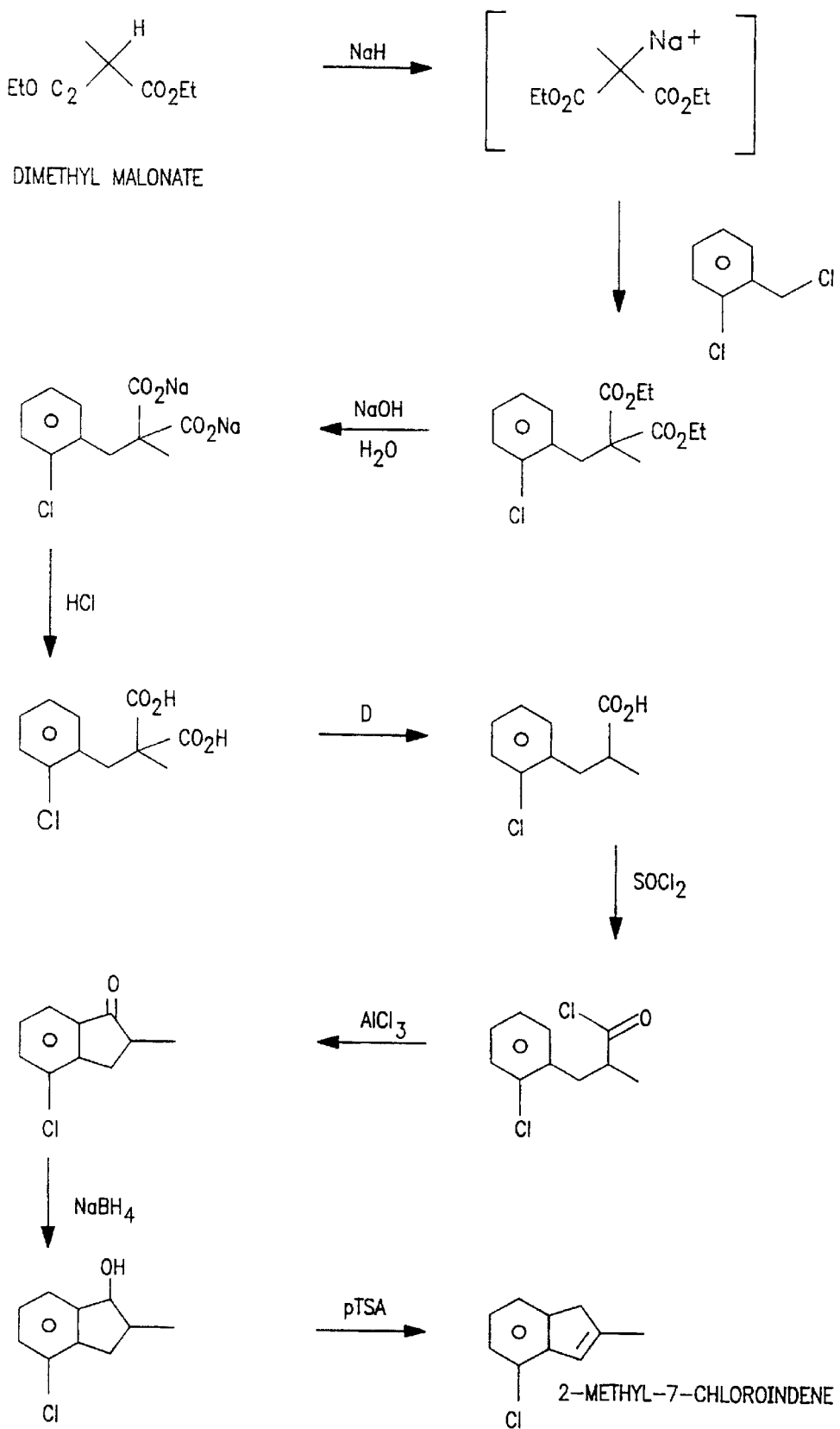
FIG. 1 illustrates a scheme for the synthesis of the Formula I compound, 2-methyl-7-chloroindene.
Figure 3:
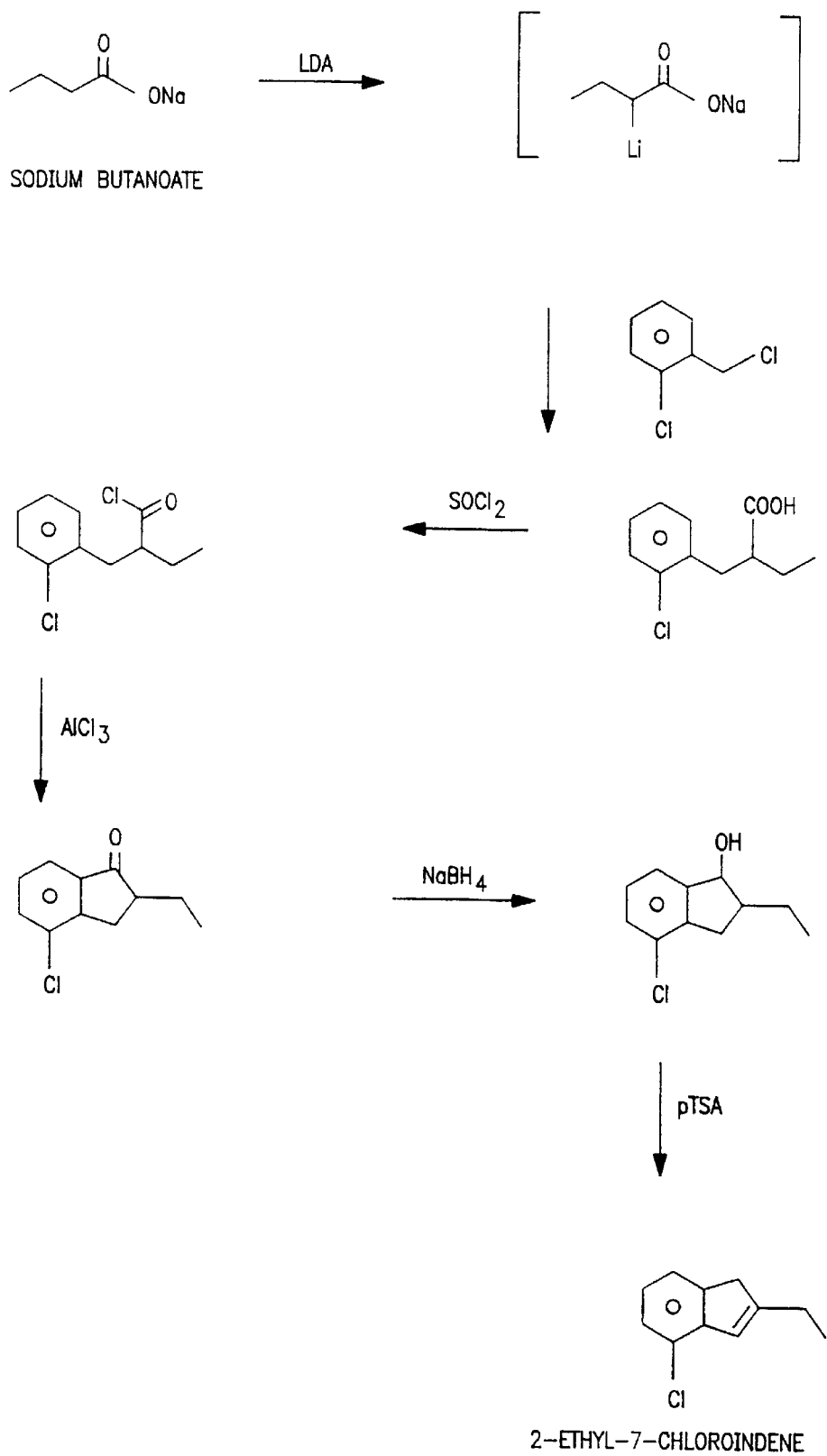
FIG. 3 illustrates a scheme for the synthesis of the Formula I compound, 2-ethyl-7-chloroindene.

Either of two methods, as shown by Examples 1 and 2 and FIGS. 1 and 3, may be used to prepare Formula I compounds.

THE EXAMPLE 1 METHOD

The starting material for the Example 1 method is a malonic acid diester having the Formula III:

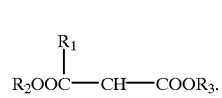

III in which $R_1$ (which is the same $R_1$ as in the Formula I and II compounds), $R_2$ and $R_3$ are the same or optionally different straight or branched chain alkyl groups having 1 to 10 carbon atoms. Alkyl groups specifically useful in this aspect of the invention include methyl, ethyl, propyl, isopropyl, butyl, isobutyl, pentyl, isopentyl, hexyl, isohexyl, heptyl, isoheptyl, octyl, isooctyl, nonyl, isononyl, decyl and isodecyl groups. A preferred diester is methyl diethyl malonate in which R is methyl and $R_2$ and $R_3$ are ethyl.

The malonic acid diester of Formula III is reacted with an alkali metal hydride ZH, in which Z is lithium, sodium or potassium, to provide an intermediate compound in which the "H" of the Formula III diester is replaced by Z+, e.g., Na+. This reaction is appropriately carried out by adding a 40% to 60% dispersion of an alkali metal hydride in mineral oil to a non-interfering solvent such as tetrahydrofuran (THF) in a reaction vessel positioned in an ice bath. The malonic diester is added slowly while the temperature is maintained below 10° C. Hydrogen evolution is monitored. Upon completion of the addition of the diester, the reaction vessel is removed from the ice bath, and the reaction mixture containing the intermediate compound is stirred, e.g., for about 1 to 4 hours, preferably about 2 hours.

When the addition is complete, the reaction mixture containing the intermediate compound is cooled to a temperature of 0° C. to 10° C., preferably 5° C., and a 2-halobenzylhalide, preferably a 2-chloro or 2-bromobenzyl halide, is added over a time period of 0.5 to 1.5 hours to provide a reaction mixture containing a Formula IV compound. This reaction mixture is stirred, preferably at about ambient temperature, for 6 to 15, preferably about 12, hours:

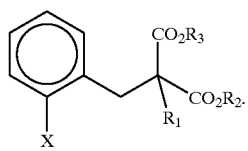

IV in which X is the halogen substituent, preferably chlorine, of the Formula I compound. The Formula IV diester is saponified by heating. The reaction mixture containing the diester is heated and combined with 30% to 60% aqueous alkali metal hydroxide, preferably NaOH, to provide a compound having Formula V:

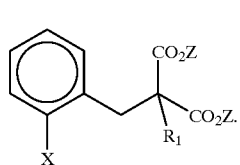

V in which Z is an alkali metal.

THF and the alcohols $R_2OH$ and $R_3OH$, which result from saponification of the diester IV, are removed by distillation. The saponification reaction mixture is cooled, and poured into aqueous acid, e.g., 4–6N HCl, with vigorous stirring to produce a compound having Formula VI:

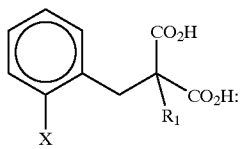

VI

The white solids comprising the Formula VI compound which form are removed by filtration, dried and placed in an appropriate reaction vessel equipped for short path distillation. Heating is applied to melt the solids and thereafter increased to 120° C. to 150° C. for a period of about 0.5 to 1.5 hours to accomplish decarboxylation and produce a compound of Formula VII:

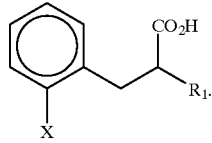

VII

The melt so produced is cooled to about 50° C., dissolved in a non-interfering solvent, e.g., an aliphatic hydrocarbon solvent having 6 to 9 carbon atoms, preferably heptane, and the Formula VII compound present in the solution is reacted with $SOCl_2$ at a temperature of 40 to 60° C. with stirring to produce a Formula VIII compound:

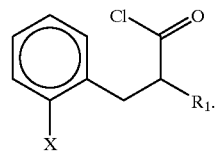

VIII

The temperature of the reaction mixture is thereafter raised to 100° C. to 130° C. to remove excess $SOCl_2$ and solvent. The reaction mixture is then cooled to room temperature, a chlorinated hydrocarbon solvent, preferably methylene chloride, is added, and the mixture is cooled to −10° C. to 0° C., followed by the addition of aluminum chloride with stirring to produce a compound of Formula IX by Friedel-Craft acylation:

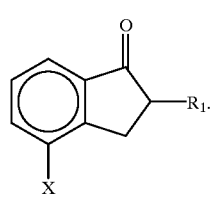

IX

The acylation reaction is quenched by pouring on to ice. The layers which form are separated, and organic layer washed with an aqueous base, preferably sodium bicarbonate. All solvent is removed by distillation, methanol is added, and the reaction mixture containing Formula IX is cooled in an ice bath and combined with sodium borohydride to produce Formula X:

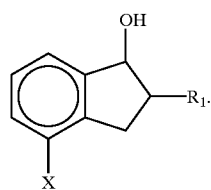

X

The reaction is quenched with water, and methylene chloride is added to separate the Formula X compound, and the solvent is removed by distillation. The Formula X compound is reacted with paratoluene sulfonic acid (pTSA) in toluene (or other aromatic solvent such as xylene or mesitylene) to afford the desired 2-substituted, 7-haloindene, compound of Formula XI:

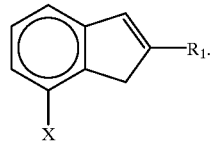

XI

Aqueous and organic layers separate upon addition of aqueous sodium bicarbonate. The organic layer is dried over anhydrous $Na_2SO_4$. Toluene is removed by distillation.

EXAMPLE 1

Synthesis of 2-Methyl-7-Chloroindene. This example illustrates the scheme depicted by FIG. 1.

Figure 2:
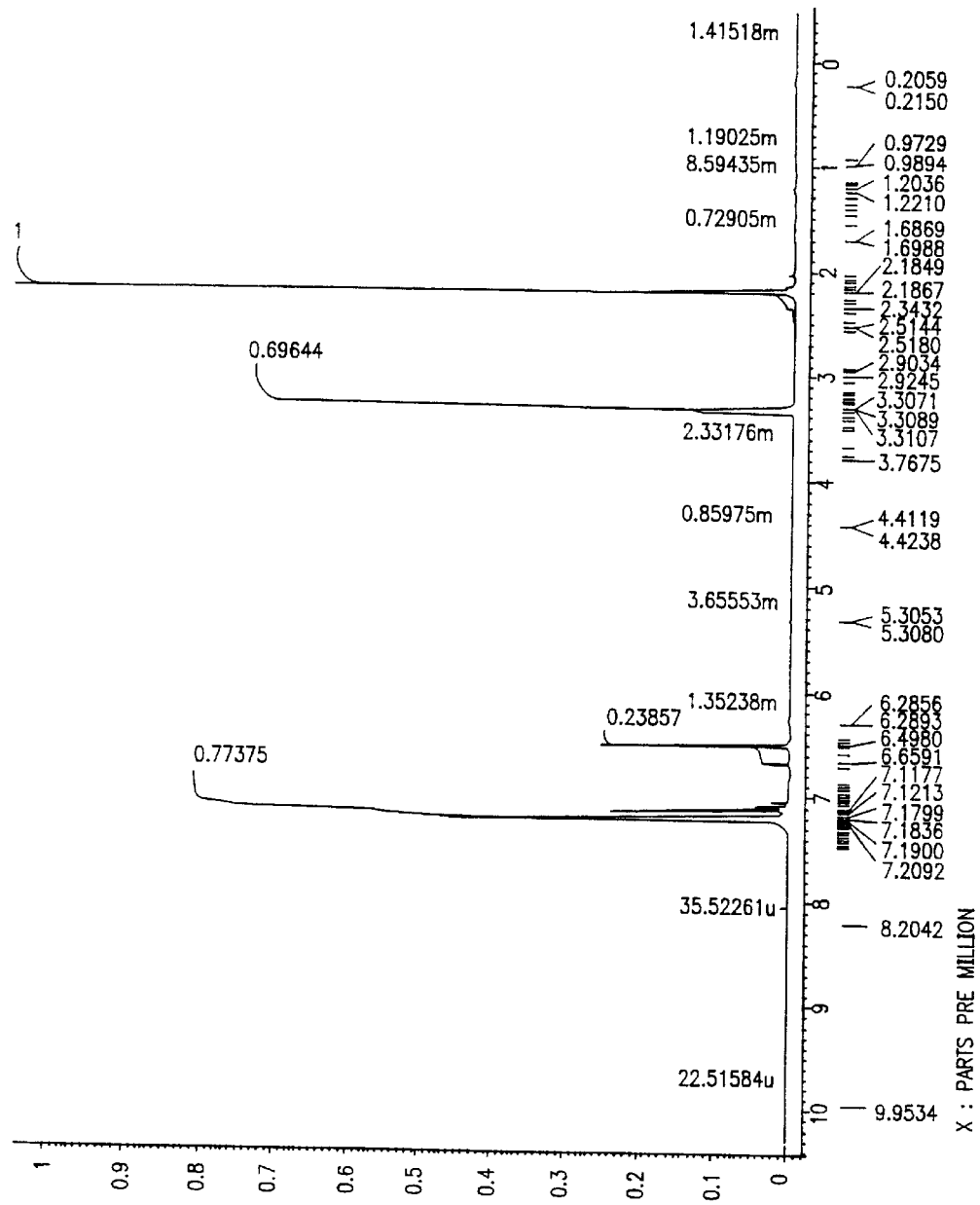
FIG. 2 is a NMR spectrum of 2-methyl-7-chloroindene produced by the FIG. 2 scheme as shown by Example 1.

A 5L round-bottom flask is equipped with a mechanical stirrer, thermometer and reflux condenser, and swept thoroughly with nitrogen. 2L tetrahydrofuran (THF) is added to the flask and then 116 g NaH, 60% dispersion in mineral oil (2.9 mol). An ice bath is applied to the flask and moderate stirring begun. 506 g methyl diethyl malonate (2.9 mol) is added slowly from an addition funnel maintaining the temperature below 10° C. Hydrogen evolution is monitored and vented through a mineral oil bubbler and controlled by the rate of addition of the methyl dimethyl malonate. Once the addition is complete, the cooling bath is removed, and the reaction stirred for 2 hours. The flask is again cooled to 5° C. and 367 mL 2-chlorobenzylchloride (2.9 mol) added over 1 hour, then stirred for 12 hours at ambient temperature. Reflux condenser is changed to short path distillation. 520 mL 50% W/v NaOH(aq) and 1500 mL $H_2O$ is added, then heating begun to distill the THF. Distillation was continued to 100° C. with additional water to keep the reaction clear and fluid. Distillation was continued to remove ethanol and water at 100° C. for 15–30 minutes. Once cooled, the reaction mixture was poured into 1.5L $H_2O$ and 1L 12N HCl with vigorous stirring. White solids, which formed immediately, were collected by filtration and dried on the Buchner funnel by aspiration for 15 minutes, then returned to the 5L flask equipped for short path distillation. Heating was applied slowly to melt the solids, and then increased to 135° C. for at least 1 hour. $CO_2$ evolution was monitored by venting through a mineral oil bubbler. The melt was cooled to 50° C. and 2L heptane added, then warmed to 45° C., and addition of 265 mL $SOCl_2$ (3.63 mol) was begun. Adequate venting was provided. After all the $SOCl_2$ was added, the reaction was stirred for 1.5 hours at 60° C., then heated to 120° C. to distill the excess $SOCl_2$ and all the heptane. The reaction flask was allowed to cool to ambient temperature and 1.5L $CH_2Cl_2$ is added. Cooling was applied to −5°–0° C., and 465 g $AlCl_3$ (3.5 mol) added in portions. The reaction was stirred at ambient temperature for 2 hours, then quenched by pouring onto 2 Kg ice. The layers were separated, and the organic layer was washed with 500 mL $H_2O$, and then 250 mL 5% w/v $NaHCO_3$ (aq). All the solvent was distilled to a temperature of 70° C. 1L methanol was added to the oil, the flask cooled with an ice bath, and a slurry of 56 g $NaBH_4$ (1.5 mol) in 500 mL methanol containing 1 g $NaOCH_3$ was slowly added. Hydrogen evolution was monitored by venting through a mineral oil bubbler and controlled by the rate of addition. The reaction was quenched by adding 1.5L $H_2O$ and 500 mL $CH_2Cl_2$ to separate the product. Solvent was distilled from the separated organic layer up to 70° C. 1.5L toluene was added to the oil and the 5L flask equipped with a Dean-Stark trap. Heating was begun and p-toluene sulfonic acid was added in 1–3 g portions. The reaction was followed by GC until the dehydration was complete. 1.5L 5% w/v $NaHCO_3$ (aq) was added to the reaction, the layers separated, and the organic layer dried over anhydrous $Na_2SO_4$. Toluene was distilled under reduced pressure to 90° C. and the product, 2-methyl-7-chloroindene, obtained by distillation thorough a 30 cm packed column at 93–5° C. at 1–3 mm Hg. Yield was 310 g (1.89 mol), 65%, of a clear, colorless oil b.p. 229° C. FIG. 2 was the NMR spectrum of the product.

THE EXAMPLE 2 METHOD

The starting material for the Example 2 method for producing Formula I compounds is an alkali metal, preferably sodium, salt of a fatty acid, e.g., butanoic acid, having the Formula $R_1COOZ$ (XI) in which $R_4$ is a 1 to 9 carbon atom straight or branched chain alkyl group as previously described and Z is an alkali metal.

This Formula XI acid is reacted in THF solution with an alkali metal, preferably lithium diisopropylamide, to form the intermediate XII:

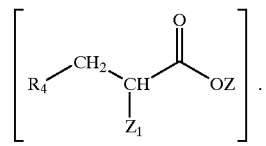

XII in which Z is an alkali metal, preferably sodium, and $Z_1$ is an alkali metal, preferably lithium.

The Formula XII compound is reacted with a 2-halobenzylhalide to provide Formula XIII compound:

XIII in which X is a halogen, preferably chlorine or bromine, i.e., the halogen of a Formula I compound.

More specifically, this series of reactions may be carried out by combining an alkali salt of a fatty acid having 2 to 10 carbon atoms with an alkali metal, preferably lithium diisopropylamide to produce a compound having the Formula XII in THF solution. The reaction is conducted at ambient temperature and preferably stirred for 24 hours. 2-halo benzylhalide is added to the reaction mixture so produced, and the reaction mixture stirred for an additional time period, preferably 18 to 24 hours. The reaction is then quenched, e.g., by the addition of water. The aqueous layer is neutralized by a mineral acid, e.g., hydrochloric acid, at which point a phase separation occurs. A 2-halobenzyl fatty acid, such as the compound of Formula XIII, is concentrated in the organic layer.

Synthesis of 2-Ethyl-7-Chloroindene is completed by the same sequence of reactions as described in Example 1 and shown in FIG. 3, beginning with the addition of $SOCl_2$.

EXAMPLE 2

Synthesis of 2-Ethyl-7-Chloroindene. This example illustrates the scheme depicted by FIG. 3.

A 12L round-bottom flask was equipped with a mechanical stirrer, thermometer and reflux condenser. 385 g sodium butanoate (3.5 mol) and 2L THF were added to form a slurry. 2.625L lithium diisopropylamide, 2M in heptane/THF/ethyl-benzene (5.25 mol, 50% excess) were added at ambient temperature, and then stirred for 24 hours. Then 705 g 2-chlorobenzyl chloride (4.375 mol, 25% excess) was added, and the reaction stirred for another 24 hours. Once completed, the reaction was quenched by adding 1500 mL $H_2O$, and the solution allowed to separate. The aqueous layer, pH=13, was separated and neutralized by addition of 12N HCl to obtain pH=7.0, at which point a phase separation occurs. 2-(2-chlorobenzyl) butanoic acid was concentrated in the organic layer. Synthesis of 2-ethyl-7-chloroindene was completed by the same sequence of reactions and method as described in Example 1, beginning with the addition of $SOCl_2$. See FIGS. 1 and 3. The product, 2-ethyl-7-chloroindene, was obtained by distillation at 110–114° C. under 1–3 mm Hg. Yield was 205 g (33% overall) of a clear, colorless oil.

PREPARATION OF FORMULA II COMPOUNDS

Figure 4:
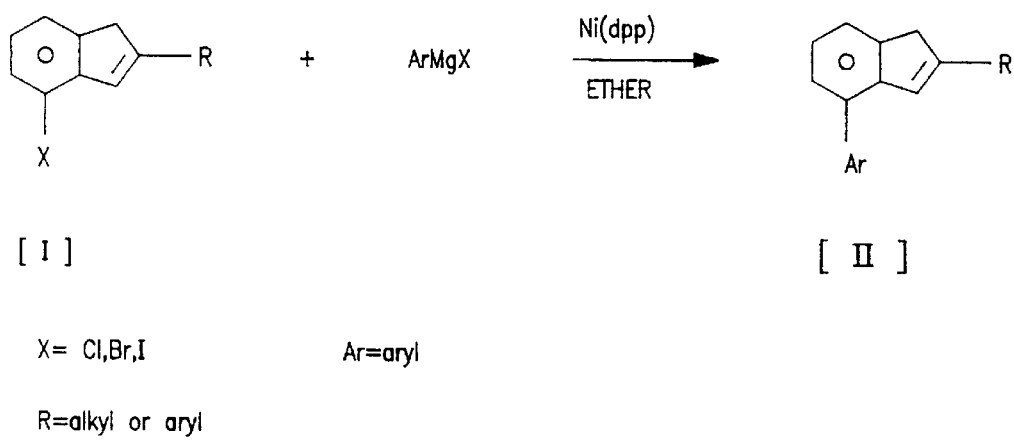
FIG. 4 illustrates a scheme for Grignard reagent coupling a Formula I compound to provide a Formula II compound.

As shown by FIG. 4, Formula II compounds are prepared in known manner by reacting a Formula I compound with a Grignard reagent, ArMgX, in which X is Cl, Br or I, Ar is any aryl group, for example, a phenyl or naphthyl group, in an ethyl ether solvent containing 1-3-bis (diphenylphosphino) propane nickel II chloride, Ni (dpp).

Examples 3–6 utilize the synthesis of the Formula II compounds depicted by FIG. 4.

EXAMPLE 3

A 5L round bottom flask was equipped with mechanical stirring, a reflux condenser and ice bath. 488.2 g distilled 7-chloro-2-methylindene (2.97 mol) was added, dissolved in 2L ether and 32.2 g Ni(dpp) (0.059 mol, 2 mol %) slurried in the solution, and stirred to cool to 0–2° C. 1.05L of 3.1M phenylmagnesium bromide in ether (3.25 mol, 10% excess) was added slowly from an addition funnel so that the temperature remained below 5° C. Once complete, the ice bath was removed, and the reaction stirred up to room temperature. The reaction was refluxed for 8 hours, and checked for completion by GC. The reaction flask was cooled with an ice bath, and 250 mL water added, then 1L 10% HCl. The aqueous and organic layers are separated, and the organic layer dried over anhydrous $Na_2SO_4$. Ether was distilled, and the residual oil placed on a column of 100 g silica gel. Elution with hexane was performed, the hexane distilled under reduced pressure to a temperature of 90° C. 2-methyl-7-phenylindene (Spaleck compound 13a) was obtained by distillation at <1 mm Hg with a 36 cm Vigreux column at 125° C. A fore-cut containing biphenyl was obtained at 70–90° C. and discarded. Yield was 507.8 g (2.47 mol) equal to 80%.

EXAMPLE 4

A 12L flask equipped as in Example 3 was charged with 661 g distilled 2-methyl-7-chloroindene (4 mol), 2.5L ether, and 43.3 g Ni(dpp) (0.08 mol, 2 mol %). 1.75L of 2.6M phenylmagnesium bromide in ether (4.55 mol, 12% excess) was added at 2° C. Following stir-out to ambient temperature and reflux for 8 hours, the reaction was quenched and worked up by the method described in Example 3. Yield of 2-methyl-7-phenylindene was 642.7 g (3.12 mol) equal to 78%.

EXAMPLE 5

A 5L flask was equipped as in Example 3. 178 g 2-ethyl-7-chloroindene (1 mol), 1L ether and 10.8 g Ni(dpp) (0.02 mol, 2 mol %) added, followed by 355 mL of 3.1M phenylmagnesium bromide in ether (1.1 mol, 10% excess). After quenching and work-up by the method described in Example 3, 176 g 2-ethyl-7-phenylindene (0.8 mol) was obtained by vacuum distillation at 140° C. in 80% yield.

EXAMPLE 6

A 5L flask was equipped as described in Example 3. 164 g 2-methyl-7-chloroindene (1 mol) 500 mL ether and 10.8 g Ni (dpp) added. 2L of 0.5M naphthyl magnesium bromide in ether was added at 20° C. The reaction was stirred vigorously at reflux for 12 hours, then quenched and worked up as described in Example 3. 184.3 g 2 -methyl-7-(l-naphthyl) indene (Spaleck compound 21) (0.72 mol) was obtained by recrystallization from heptane in 72% yield.

METALLOCENE CATALYSTS

The Formula II compounds of this invention may be converted to metallocene α-olefin polymerization catalysts in the manner illustrated by Spaleck's Schemes 1 and 2. Such catalysts may have the formula XIV

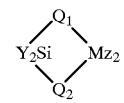

wherein $Q_1$ and $Q_2$ are the same or different Formula II compounds, Y is an alkyl group, for example, an alkyl group having 1 to 5 carbon atoms, M is a group IV metal and Z is a halogen. $Y_2Si$ is preferably $(CH_3)_2$ Si and $MZ_2$ is preferably $ZrCl_2$.

Example 7 illustrates one such conversion.

EXAMPLE 7

A 1L flask was charged with toluene (300 mL), THF (15 g, 0.2 mol) and 2-methyl-4-naphthyl-indene (52 g, 0.2 g). The contents were cooled to −20° C. and 1.6 M butyllithium in hexane (125 mL) was slowly added. This mixture was warmed to 25° C. and stirred for four hours. The contents were cooled to −20° C. and dimethyldichloro-silane (12.9 g, 0.1 mol) was added. This reaction mixture was warmed to 25° C. and stirred for twenty-four hours. Distil the reaction mixture under reduced pressure to pot temperature of 45° C. Allow the reaction to cool to ambient temperature and add ether (15 g, 0.2 mol). The reaction mixture was then cooled to −20° C. and 1.6 M butyllithium in hexanes (125 mL, 0.2 mol) was slowly added. This reaction mixture was slowly warmed to 25° C. and stirred for twenty-four hours. Cool the reaction to −30° C. and add zirconium tetrachloride, $ZrCl_4$ (23.2 g, 0–1 mol). The reaction is added to warm to ambient temperature and stirring continued for another twelve hours.

The reaction mixture was then filtered and the solids were washed with hexane. The solids were dried under vacuum. The dry solids were dissolved in dichloromethane (800 mL) and this solution filtered through a small bed of celite to remove lithium chloride. The volume was reduced to 100 mL by solvent removal. The filtered crystals were washed with 10–15 mL dichloromethane and then dried in vacuum. The retained yield—60–80 g 2 methyl-4-naphthyl-indene-Si $(CH_3)_2$ -4-napthyl-2-methyl indene.

What is claimed is:

1. The method comprising reacting a compound having Formula I

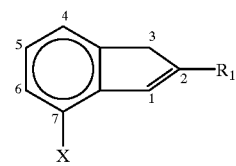

in which $R_1$ is any straight or branched chain alkyl group having 1 to 10 carbon atoms, and X is a halogen with ArMgX in which Ar is any aryl group and X is a halogen wherein a compound having Formula II

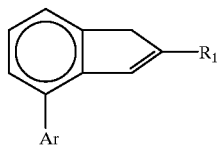

is produced.

2. The claim 1 method in which Ar is a phenyl, a napthyl or a 9-fluorenyl group.

3. The claim 1 or claim 2 method in which X is chlorine or bromine or fluorine.

4. The claim 1 or claim 2 method in which $R_1$ is a methyl, ethyl, propyl, isopropyl, butyl, isobutyl, hexyl, isohexyl, octyl or isooctyl group.

5. A method for synthesizing a compound having Formula I

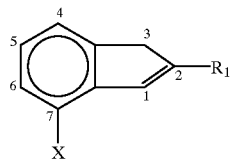

which $R_1$ is any straight or branched chain alkyl group having 1 to 10 carbon atoms, and X is a halogen which comprises:

(i) reacting a malonic acid diester with an alkali metal hydride and a 2-halobenzylhalide to produce a compound having Formula IV

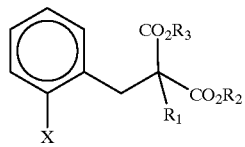

wherein $R_2$ and $R_3$ are the same or optionally different straight or branched chain alkyl groups having 1 to 10 carbon atoms;

(ii) saponifying said compound having Formula IV to produce a compound having Formula V

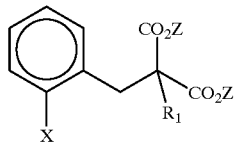

in which Z is an alkali metal;

(iii) converting said compound having Formula V to a compound having Formula VII

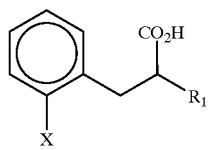

(iv) reacting said compound having Formula VII with $SOCl_2$ to produce a compound having Formula VIII

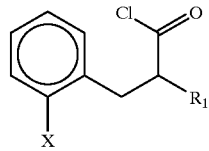

(v) reacting said compound having Formula VIII with aluminum chloride to produce a compound having Formula IX (vi) reacting said compound having Formula IX with sodium borohydride to produce a compound having Formula X and (vii) reacting said compound having the Formula X with paratoluene sulfuric acid to produce said compound having Formula I.

6. The claim 5 method in which:

(i) said malonic acid diester of step (i) has the Formula III

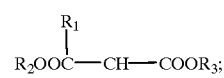

and (ii) the alkali metal hydride of step (i) is sodium hydride, and the halobenzylhalide of step (i) is 2-chlorobenzyl chloride.

7. A method which comprises:

(i) reacting an alkali metal salt of a fatty acid having 1 to 10 carbon atoms with an alkali metal hydride to produce a first reaction mixture containing an intermediate compound; and (ii) combining said step (i) reaction mixture with a 2-halobenzylhalide to convert said intermediate compound into a compound having the Formula XIV

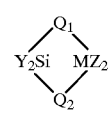

8. The method which comprises reacting a compound having the formula:

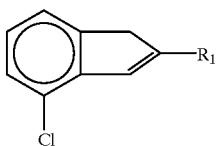

in which $R_1$ is a straight or branched chain alkyl group having one to ten carbon atoms with a naphthyl magnesium bromide wherein a reaction mixture containing a compound having the Formula

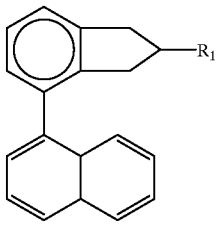

in which $R_1$ is a straight or branched chain alkyl group is produced.

9. The claim 8 method in which $R_1$ in the compound having the formula:

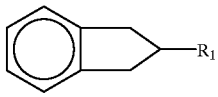

is methyl or ethyl.

10. A method which comprises reacting 7-chloro-2-methylindene with naphthyl magnesium bromide, wherein a reaction mixture containing 7-naphthyl 2-methylindene is produced.

11. The claim 10 method in which said 7-naphthyl-2-methylindene is separated from said reaction mixture.

12. A method which comprises
(i) reacting a compound having Formula I

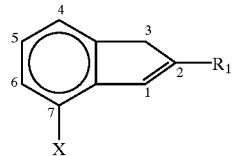

in which $R_1$ is any straight or branched chain alkyl group having 1 to 10 carbon atoms, and X is a halogen with ArMgX in which Ar is any aryl group and X is a halogen wherein a compound having Formula II

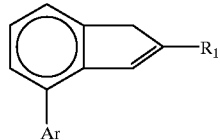

is produced; and
(ii) converting said compound of Formula II produced in step (i) to a compound having the formula XIV

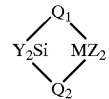

wherein $Q_1$ and $Q_2$ are the same or different Formula II compounds, Y is an alkyl group, M is a group IV metal and Z is a halogen.

13. The claim 12 method wherein Y is methyl and Z is chlorine.

* * * * *